(12) United States Patent
Noras

(10) Patent No.: US 9,913,597 B2
(45) Date of Patent: Mar. 13, 2018

(54) COIL ARRANGEMENT FOR A MAGNETIC RESONANCE TOMOGRAPHY DEVICE

(71) Applicant: Hubert Noras, Würzburg (DE)

(72) Inventor: Hubert Noras, Würzburg (DE)

( * ) Notice: Subject to any disclaimer, the term of this patent is extended or adjusted under 35 U.S.C. 154(b) by 415 days.

(21) Appl. No.: 14/646,056

(22) PCT Filed: Nov. 15, 2013

(86) PCT No.: PCT/DE2013/100386
§ 371 (c)(1),
(2) Date: May 20, 2015

(87) PCT Pub. No.: WO2014/079416
PCT Pub. Date: May 30, 2014

(65) Prior Publication Data
US 2015/0305647 A1    Oct. 29, 2015

(30) Foreign Application Priority Data
Nov. 22, 2012   (DE) .................. 10 2012 022 779

(51) Int. Cl.
*A61B 5/055*    (2006.01)
*A61B 5/00*    (2006.01)
(Continued)

(52) U.S. Cl.
CPC ............ *A61B 5/055* (2013.01); *A61B 5/4381* (2013.01); *G01R 33/30* (2013.01);
(Continued)

(58) Field of Classification Search
CPC ..... A61B 5/055; A61B 5/0555; A61B 5/4381; G01R 33/30; G01R 33/34084; G01R 33/3415; G01R 33/385; G01R 33/54
See application file for complete search history.

(56) References Cited

U.S. PATENT DOCUMENTS

2003/0197508 A1* 10/2003 Tamura .............. G01R 33/3678
324/318
2009/0216110 A1* 8/2009 Piron .................... G01R 33/36
600/415
(Continued)

FOREIGN PATENT DOCUMENTS

DE          10317629 A1    11/2003
DE          10221644 A1    12/2003
DE      102011075440 A1    11/2012

OTHER PUBLICATIONS

International Search Report (ISR) with regard to PCT/DE2013/100386 as completed by the EPO dated Jan. 20, 2014 and dated Jan. 29, 2014.

*Primary Examiner* — Mark Remaly
(74) *Attorney, Agent, or Firm* — Westman, Champlin & Koehler, P.A.

(57) ABSTRACT

A magnetic resonance imaging device for prostate examinations with a patient in said device comprises a coil for generating a strong homogeneous magnetic field in the direction of the longitudinal axis of the patient, at least one transmission coil for generating an electromagnetic alternating field, three gradient coils and suitable reception coils, of which individual coils are arranged below the patient in the lower back region and/or at the rear part and at least one of said coils is arranged above the patient, and also comprises data processing for obtaining images from the signals of the transmission and reception coils, wherein a closed reception coil is provided which sits closely against the patient and surrounds the scrotum and the penis.

16 Claims, 2 Drawing Sheets

(51) Int. Cl.
   *G01R 33/34*      (2006.01)
   *G01R 33/30*      (2006.01)
   *G01R 33/385*     (2006.01)
   *G01R 33/54*      (2006.01)
   G01R 33/3415     (2006.01)

(52) U.S. Cl.
   CPC ..... *G01R 33/34084* (2013.01); *G01R 33/385* (2013.01); *G01R 33/54* (2013.01); *A61B 5/0555* (2013.01); *G01R 33/3415* (2013.01)

(56) References Cited

U.S. PATENT DOCUMENTS

2010/0253351 A1      10/2010  Huish
2012/0283550 A1 *    11/2012  Driemel ................. G01R 33/30
                                                                600/415
2015/0177346 A1 *     6/2015  Mazurewitz ..... G01R 33/34084
                                                                324/309

* cited by examiner

Figur 1

COIL ARRANGEMENT FOR A MAGNETIC RESONANCE TOMOGRAPHY DEVICE

The invention relates to a magnetic resonance tomography device for prostate examinations having a patient therein, comprising a coil for generating a strong homogeneous magnetic field in the direction of the longitudinal axis of the patient, at least one transmitter coil for generating an electromagnetic alternating field, three gradient coils and suitable receiver coils, individual ones of which are arranged below in the lower back region and/or at the backside and at least one is arranged above the patient, as well as data processing for imaging from the signals of the transmitter and receiver coils.

The early recognition of, in particular, prostate cancer is important for successful treatment. The normal method of searching for prostate cancer, such as manual examinations and blood tests, fail in locating some malignant tumours or sometimes give a false positive test result. Biopsy is the method of locating a tumour and assessing its danger. Unfortunately this biopsy often misses the tumour.

Magnetic resonance tomography is an imaging process with excellent soft tissue contrast; bones, on the other hand, are not distinctly imaged. It is therefore used for investigating the prostate, wherein the best possible resolution is to be obtained.

Magnetic resonance tomography is based on the principles of nuclear spin resonance (NMR), in particular pulsed field-gradient NMR, and is therefore also known as nuclear spin tomography. With the aid of magnetic resonance tomography, cross-sectional images of the human (or animal) body can be produced, which make possible an assessment of the organs and many pathogenic organ changes. Magnetic resonance tomography requires a very strong static magnetic field and electromagnetic alternating fields in the radio frequency range, with which particular atomic nuclei (actually always the hydrogen nuclei) in the body are excited in resonance, which then emit and induce electrical signals in the receiver electrical circuit. To achieve the local resolution, gradient coils are used, which serve to generate the magnetic gradient fields. The gradient coils are used in pairs with the same electrical current strength but opposite polarity, so that one coil reduces the static magnetic field, while the opposite coil increases it by the same amount. As a result, the magnetic field is provided with a linear gradient. Such a device exists for all three spatial directions. The background is that the local magnetic field determines the resonance frequency and thereby makes possible spatial localisation. In the prior art, planar receiver coils are normally used, that is to say at least one planar coil element lies beneath the torso of the patient and a planar coil element lies on the patient. Typically these coil elements consist in each case of six coils, wherein a preamplifier is usually present for each coil.

These so-called phase-array coils are a combination of a plurality of surface coils in an array. The idea is, with relatively small coils that have a good signal-to-noise ratio, nevertheless to cover a large area. The noise is composed of the thermal noise of the object to be measured and the thermal noise of the high-frequency coil.

However these receiver coils are, by virtue of the construction, relatively remote from the prostate. As a result, only a relatively inadequate resolution of the prostate is ensured. Furthermore, to improve the spatial resolution, a so-called endorectal coil is already used, which permits a better spatial resolution of the prostate, since in this case the coil can be positioned in the direct vicinity of the prostate.

It is the object of the invention to provide a device with which, without the necessity to use an endorectal coil, the spatial resolution of the prostate is nevertheless decisively increased.

To solve this object, a closed coil is provided, which encloses the scrotum and penis.

The coil is thereby positioned in the direct vicinity of the prostate and thereby permits a better spatial resolution, since it can intercept more signals from the volume element of the prostate. This novel coil is used in combination with a conventional planar coil element on the back of the patient. Actually the patient would have to be surrounded on all sides with receiver coils to intercept as much of the signal as possible, that is to say receiver coils would also be appropriate at the sides. However, because of the different anatomies of patients' bodies, this is difficult to implement in practice. In the case of slim patients, a relatively large circumferential angle of the standard coil element is covered, that is to say the signal amount that is lost is smaller since the distance between the upper and lower side of the patient is smaller; a better resolution is thus achieved here. In the case of relatively fat patients, the circumferential angle that is covered by the standard coil element is smaller, that is to say more signal is lost at the sides. Consequently, the resolution is worse than in the case of the slim patient. The obvious solution would be to provide different standard coil elements for different patients, though this is not practicable.

An optimum image quality can then be achieved if the receiver coil surrounding the testicles is oriented with its surface normal in the direction of the prostate. The term "surface normal" is already not unambiguous for flat coils, since there exists a multiplicity of surface normals oriented parallel to one another. Since, in the case of curved coils, it is still the case that the surface normals, which are defined as perpendicular in the individual points of the surface, that is to say perpendicular to the tangential plane extending there, have different orientations, for the unambiguous determination of the profile of the surface normal, that one should be selected that runs through the centroid of the surface of the receiver coil, so that, as a result, a clear instruction for action is provided.

In a concrete embodiment, three coils are arranged in a triangle above the patient, that is to say that two coils lie parallel side by side on the abdomen of the patient and the third coil encloses the scrotum and penis. The third coil lies with the lower longitudinal sides in a V-shape at the right and left strip, so that the scrotum and penis pass through the opening of the coil. By spreading the thighs and with a slight pressure of the coil, an optimum orientation of the coil element is obtained. The two upper coil elements are located between the strip and the lower abdominal wall and can be oriented with their surface normal in the direction of the prostate.

In an alternative embodiment, the magnetic resonance tomography coil can also be constructed of more than three coils on the upper side of the patient. Thereby, the resolution capacity can be increased since the signal-to-noise ratio is better for smaller coils. The number of coils, in its totality, defines the surface area in which signals can be registered and thereby also evaluated. Here, the outer perimeter of this area, which adds up to the total of the surface areas of the individual coils, determines the penetration depth of the entire arrangement, which is formed from all coils. If a plurality of coils are used together and simultaneously, a measurement result is obtained which combines the high sensitivity of the individual coil on one hand and the high penetration depth of the entire arrangement on the other hand.

The relative assignment of the coils is in principle arbitrary within the scope of the invention. The coils can thus be spaced from one another, which may also be necessary from constructional constraints. It is to be seen as disadvantageous that signals emitted in the interstices of the coil cannot be used.

In a preferred case, the coils are directly adjacent to one another, which has the advantage that as few emitted signals as possible are lost. The higher the received intensity of the signals, the better is the image quality.

The laying on and removal are greatly simplified if the coils are accommodated in a flexible mat. This has the advantage that this mat largely conforms to the individual body form of the patient. The receiver coils thus lie as close as possible to the patient and thus permit a better image quality. A passage for the penis and scrotum must be present in the mat.

The aim is to distinctly image the volume element surrounding and representing the prostate. For optimization, the radius of the receiver coil is chosen such that it is larger than or equal to the average distance of the coil plane from the organ to be examined, in this case the prostate.

The distance varies from patient to patient; the term "average distance" is therefore described here as the mean value of anatomical conditions. The penetration depth depends directly on the coil radius. The resolution is optimum when the distance of the organ to be examined from the coil plane corresponds, at maximum, to the radius of the coil. In principle, the image quality is all the better the lower the distance from the coil to the prostate is.

It was recognised as expedient, during the imaging phase, to spatially position the patient in the region of the abdomen or of the torso, with a fixture device at least partly enclosing these. The patient is then retained with the aid of a corset so that no movements that might cause blurring of the recording are possible. Due to the fixing, a better image quality is achieved, since the movement of the patient is restricted and fewer movement artefacts can occur.

Finally, it is proposed to fasten the receiver coils via adjustment devices, which permit, in the practical application, the receiver coils to be optimally oriented in order to obtain a better image quality in consequence. An expressly recommended possibility consists in fastening the adjustment devices on the fixing device.

In an advantageous embodiment, a wedge-shaped pillow is used, which is pushed beneath the pelvis of the patient such that the pelvis is tilted slightly upwards, which requires a pushing of the wedge-point in the direction of the longitudinal axis of the patient. This cushion serves for orientation of the pelvis and therefore the orientation of the prostate with respect to the receiver coil. Through an optimum orientation, a better image quality can be achieved.

In a further embodiment, a pillow is used that can be charged with liquid or gas in order thereby to change the shape of the pillow and thereby optimize the orientation of the pelvis of the patient. By an appropriate charging of the pillow, an arbitrary orientation of the pelvis can be achieved in infinitesimal steps and in wide limits.

In one embodiment, the pillow can be subdivided into a plurality of sectors or chambers, which can be differently charged with gas or liquid. If a chamber is charged with higher pressure, it is enlarged; with lower pressure, the chamber in each case is smaller. This has the advantage that the pelvis of the patient can be oriented in different spatial directions in an accurately targeted manner by individually charging and thereby adjusting the individual chambers. The number of sectors or chambers corresponds to the number of the adjustment parameters that are available. The aim is also to improve the image quality here.

Finally, receiver coils can also be accommodated on or in this pillow. The installation of the receiver coils directly on or in the pillow permits a closer placement on the patient; this is associated with a higher resolution and a better signal-to-noise ratio.

In a further embodiment, electrical preamplifiers can be installed for each coil in order to amplify the signal actually at the coil where possible. Thereby, the additional relative noise amplitude due to the wires to the electronics of the magnetic resonance tomographic device becomes smaller, and thereby the signal quality and ultimately also the image quality are improved.

Further details and features of the invention are explained below in greater detail with reference to embodiments shown in the drawing. In schematic views.

Figure 1:
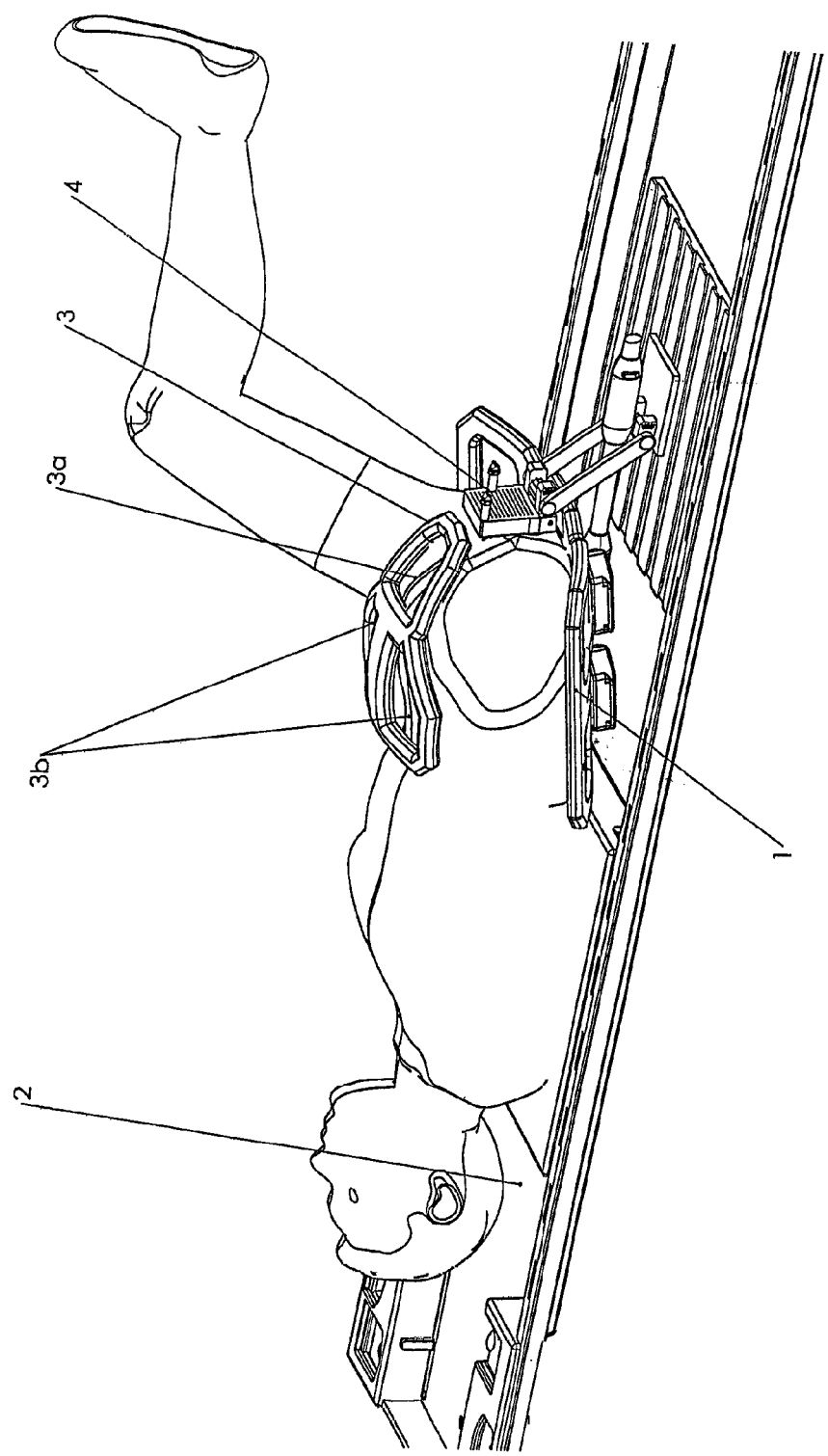
FIG. 1 shows a coil element with patient according to the invention

In the 3D representation of FIG. 1, the patient (2) is shown schematically lying on a table. Below the patient, in the lower back region and on the backside, is located a standard receiver coil element (1), which is slightly curved so that it adapts somewhat to the torso of the patient. The standard coil element (1) typically consists of six individual coils. This arrangement is also called a phased array.

On the lower abdomen region and on the groin region of the patient there is located the coil element (3) according to the invention. This is subdivided into three partial coils, which are arranged in a triangle. Two coils (3b) are located parallel next to one another on the lower abdomen region of the patient and are oriented with their surface normal in the direction of the prostate. A third coil (3a), which is of decisive importance in conjunction with the invention, was attached centrally below to these two coils (3b) so that it encloses the scrotum and penis and bears against the groin of the patient when the latter slightly spreads his thighs. This third coils (3a) if V-shaped and is also oriented with its surface normal in the direction of the prostate. The biopsy device (4), which is also shown, does not play a role for the invention. The actual magnetic resonance tomographic device, that is to say the coil generating the strong homogeneous magnetic field and the transmitter coil, is not shown. The gradient coils are also not illustrated.

Figure 2:
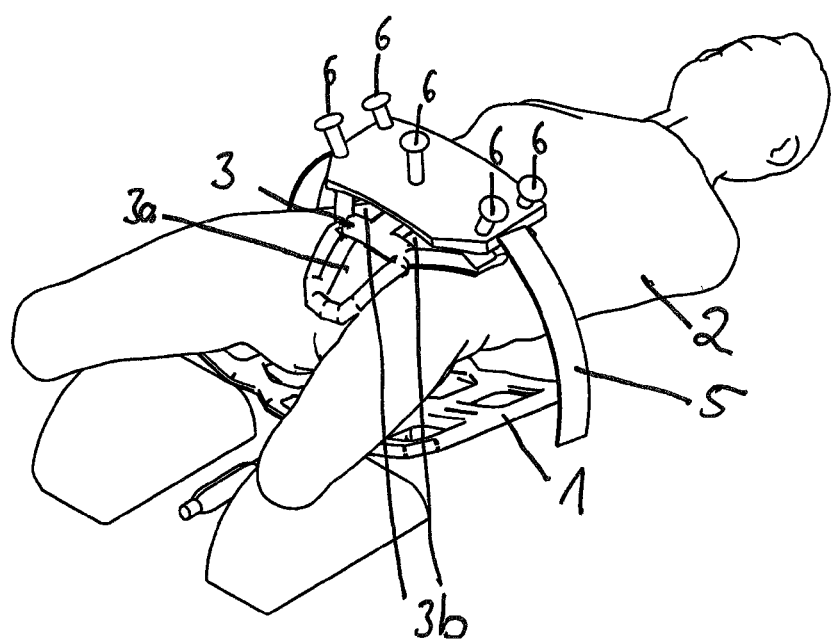
FIG. 2 shows a coil element with patient as well as a fixing device

In FIG. 2, the patient (2) is shown schematically lying down from an angle of view that is different from that in FIG. 1. An adjusting device (5) is additionally shown. Below the patient, there is located a standard receiver coil element (1), on which the patient lies with the lower back region and the backside. Directly on the lower abdominal wall and in the groin region of the patient, there is located the coil element (3) according to the invention. Towards the head, the two coils (3b) are oriented on the abdomen of the patient. In the opposite direction, there follows the third coil (3a), which encloses the penis and scrotum. The coils located above the patient are fastened on a fixing device (5), which partly circumscribes the torso of the patient in an arc. Above the two upper coils (3b), this device is adapted to the form of the coils. Five adjusting screws (6) permit, by means of adjusting devices, which are not illustrated, an optimization of the orientation of the coils (3) relative to the patient (2).

In all the diagrammatic illustrations, essential functional equipment elements are not shown for reasons of clarity. These include the homogeneous coil, the gradient coils and the data processing system necessary for evaluation.

LIST OF REFERENCE CHARACTERS

1 Standard coil element
2 Patient
3 Coils
3a Receiver coil
3b Coils
4 Biopsy device
5 Fixing device
6 Adjusting screws

The invention claimed is:

1. Magnetic resonance tomography device for human prostate examinations, comprising:
 a coil for generating a strong homogeneous magnetic field in the direction of the longitudinal axis of a patient under examination;
 at least one transmitter coil for generating an electromagnetic alternating field;
 three gradient coils and receiver coils, individual ones of the receiver coils are arranged in positions corresponding to a lower back region, a posterior, and above a patient under examination;
 data processing for imaging from the signals of the transmitter and receiver coils; and
 a closed receiver coil configured to bear against a groin adjacent a prostate, and annularly enclose a scrotum and a penis of a patient under examination.

2. Magnetic resonance tomography device according to claim 1, wherein the receiver coil annularly enclosing the scrotum of a patient under examination surrounds the testicles and is oriented with its surface normal running through a surface centroid, in the direction of the prostate of the patient under examination.

3. Magnetic resonance tomography device according to claim 1, wherein three receiver coils are arranged in a triangular configuration, and two of the receiver coils are arranged in positions corresponding to positions between the groin and a lower abdominal wall of a patient under examination.

4. Magnetic resonance tomography device according to claim 1, wherein more than three receiver coils are configured to be arranged on a patient under examination.

5. Magnetic resonance tomography device according to claim 3, wherein the receiver coils are spaced from one another.

6. Magnetic resonance tomography device according to claim 3, wherein the receiver coils are directly contiguous with one another.

7. Magnetic resonance tomography device according to claim 1, wherein the receiver coils are accommodated in a flexible mat, which is configured to lie on a patient under examination.

8. Magnetic resonance tomography device according to claim 1, wherein a receiver coil radius is larger than or equal to a typical distance of the coil plane from a prostate of a patient under examination.

9. Magnetic resonance tomography device according to claim 1, further comprising a corset attached to an examination table with straps, the corset at least partly enclosing the abdomen or the torso of the patient.

10. Magnetic resonance tomography device according to claim 1, further comprising screws or studs, which press the receiver coils toward the body of the patient.

11. Magnetic resonance tomography device according to claim 1, further comprising a wedge-shaped pillow arranged below a pelvis of a patient under examination.

12. Magnetic resonance tomography device according to claim 11, wherein the pillow is configured to be charged with a liquid or a gas is arranged below a pelvis of a patient under examination.

13. Magnetic resonance tomography device according to claim 11, wherein the pillow is subdivided into a plurality of sectors/chambers, each of which is configured to be charged with a liquid or a gas.

14. Magnetic resonance tomography device according to claim 11, wherein receiver coils are installed on or in the pillow.

15. Magnetic resonance tomography device according to claim 1, further comprising an electric amplifier for each coil.

16. A method of examining a prostate of a male patient using a magnetic resonance tomography device, the method comprising:
 supporting the patient on an examination table;
 generating a homogeneous magnetic field in the direction of a longitudinal axis of the patient using a first coil of the device;
 generating an electromagnetic alternating field using a second coil of the device;
 generating gradient magnetic fields using a third set of coils of the device;
 positioning a first receiver coil of the device on a posterior side of the patient adjacent a lower back region of the patient;
 positioning a second receiver coil of the device against the groin and adjacent the prostate of the patient, wherein the second receiver coil surrounds the scrotum and penis of the patient; and
 generating images using the device based on signals received by the first and second receiver coils.

* * * * *